(12) United States Patent
Perez

(10) Patent No.: US 8,298,181 B2
(45) Date of Patent: Oct. 30, 2012

(54) VASCULAR CATHETER INSTALLER

(76) Inventor: James Gerard Perez, Bonita, CA (US)

( * ) Notice: Subject to any disclaimer, the term of this patent is extended or adjusted under 35 U.S.C. 154(b) by 1398 days.

(21) Appl. No.: 11/557,495

(22) Filed: Nov. 8, 2006

(65) Prior Publication Data

US 2007/0233000 A1 Oct. 4, 2007

Related U.S. Application Data

(60) Provisional application No. 60/788,747, filed on Mar. 30, 2006.

(51) Int. Cl.
*A61M 5/00* (2006.01)
(52) U.S. Cl. ........................................ 604/115; 604/187
(58) Field of Classification Search .................... 604/115
See application file for complete search history.

(56) References Cited

U.S. PATENT DOCUMENTS

| | | | | |
|---|---|---|---|---|
| 4,403,987 A * | 9/1983 | Gottinger | ...................... | 604/115 |
| 5,055,102 A * | 10/1991 | Sitnik | ........................... | 604/192 |
| 6,066,116 A * | 5/2000 | Fox | ................................. | 604/115 |
| 2003/0014039 A1* | 1/2003 | Barzell et al. | ..................... | 606/1 |
| 2005/0143693 A1* | 6/2005 | Von Teichert | ................. | 604/263 |
| 2005/0273057 A1* | 12/2005 | Popov | ..................... | 604/164.08 |

\* cited by examiner

*Primary Examiner* — Nicholas Lucchesi
*Assistant Examiner* — Jason Flick

(57) ABSTRACT

A vascular catheter installer with a syringe holder adapted for use with a catheter syringe is provided for installing an indwelling catheter into a blood vessel. A syringe holder is slidably set on a rigid shaft, allowing a technician to maneuver an attached catheter syringe up and down the shaft. The technician presses down on a finger-hold platform while a stabilizer holds the device in place. The syringe holder can be locked in multiple locations along the shaft and the needle of the syringe can be immobilized within the protective walls of a needle shield for safety.

8 Claims, 7 Drawing Sheets

VASCULAR CATHETER INSTALLER

This application claims the benefit of U.S. Provisional Application No. 60/788,747 filed on Mar. 30, 2006.

BACKGROUND OF THE INVENTION

1. Field of Invention

This invention relates generally to catheter insertion devices, specifically to a vascular catheter installer device adapted for use with a catheter syringe.

2. History of Technology

In order to install an indwelling catheter into a blood vessel of a patient, a medical technician will often struggle with the fact that the targeted blood vessel may tend to move away from an incoming introducer needle. A second problem is that the needle is exposed for a substantial length of time during the procedure, limiting safety. A third problem arises when the targeted blood vessel is an artery; the artery is often difficult to locate. A fourth problem is that it is difficult for the technician to maintain a straight path of insertion. A fifth problem is that it is typically impossible to keep exposed fingers away from the puncture site. The present invention solves these problems.

An indwelling venous catheter is inserted into a targeted blood vessel of a patient by a qualified technician, typically for the purpose of infusing liquid substances into the patient or for occasionally removing venous blood from the patient. The catheter is inserted using a catheter syringe. After the catheter is inserted properly, the syringe is removed, and the catheter is secured to the patient.

Although the present invention is adapted for use with both venous and arterial catheters, for the purpose of clarity, this discussion will focus mostly on arterial catheters, also known as arterial lines, a-lines, or art lines. An arterial catheter is inserted into a selected artery of a patient by a technician, usually in a critical care environment within a healthcare facility. Arterial catheters are used typically for blood pressure monitoring and for patients who are in need of frequent arterial blood draws. A variety of catheters are available; a standard 20-gauge straight intravenous catheter is one type which is frequently used. The radial artery is the insertion site of choice, but other arterial sites may be used if necessary; these alternative sites include the femoral, brachial, ulnar, axillary, and dorsalis pedis arteries. Arterial blood sampling is achieved utilizing a separate access port placed onto the hub of the inserted catheter, and may be performed for blood collection and for blood gas analysis. Arterial blood gas analysis is performed to determine at least the partial pressures of oxygen ($PaO_2$) and carbon dioxide ($PaCO_2$), and the pH of the blood sample. These values are important in assessing pulmonary function, since these measurements indicate the status of gas exchange between the lungs and the blood.

The catheter is retained over the introducer needle of a catheter syringe. When the technician inserts the introducer needle into the artery, a flash of blood in the blood receptacle of the syringe signals the technician that proper placement of the needle within the artery has occurred. The catheter is then slid off of the introducer needle and the needle is removed from within the catheter, leaving only the catheter in the artery. The catheter hub is then connected to a transducer tubing system, and then the hub is secured to the patient's wrist.

A variation of the standard arterial catheter syringe is a syringe with a guide wire unit attached. The guide wire is used to help guide the catheter into the artery; after the technician has inserted the introducer needle properly into the artery, the technician advances the guide wire through the hollow needle and into the artery, providing a track over which the catheter can be fed into the artery.

A modified Allen Test (collateral circulation test) should always be performed by the technician before inserting a needle and catheter into a patient's radial artery. The Allen Test determines if blood is capable of flowing through the ulnar artery. The ulnar artery is the only other source of blood to the hand aside from the radial artery. A negative test result is indicative of inadequate collateral blood supply to the hand and requires the selection of another location as the site for catheter insertion.

The catheter insertion procedure is difficult and prone to errors, even when the technician has ample experience. Because of the traumatic nature of the procedure, and the large number of complications that may arise from complications, it is important for the technician to try to insert the catheter properly on the first attempt. Prior art has seriously failed to provide technicians with adequate means to insert an arterial catheter regularly on the first attempt.

An unrestrained blood vessel may tend to move away from an incoming needle, particularly in older patients whose skin has become loose and has lost elasticity. A loss of elasticity in the skin creates a loss of stability around the blood vessel, which allows the vessel to roll around under the surface of the skin. It is possible for a needle to push the vessel away from its path, causing the technician to miss the targeted vessel completely. The present invention solves this problem by providing a blood vessel stabilizer to hold the vessel in place during a catheter insertion attempt.

Currently, the technician will press her or his finger over an anticipated arterial puncture site and then estimate where the artery lies under that finger; it is a rough estimate and the technician often miscalculates. Alternatively, the technician may place two fingers over the artery and attempt to hold the artery in place between the fingertips, inserting the needle between the two fingertips to attempt to penetrate the artery. This method has its limitations; the technician should have a tight pair of gloves, cannot have long finger nails, and will rely on bulky finger tips to pinpoint a relatively thin artery between them, and this technique is impossible to use on infants and small children. The present invention uses a blood vessel stabilizer to hold the artery within two integrated stabilizer fingers at the base of the device, and it partially occludes the artery during use; this creates a stable and augmented pulse at the site where the needle will enter the artery, simplifying palpation of the artery and vastly diminishing the labor involved in identifying where to insert the needle. A blood vessel stabilizer further allows the technician to keep any exposed extremities away from the puncture site while inserting the needle into the site, thus improving safety.

Because of low blood pressure, a patient's pulse may be weak and hard to locate. It is sometimes necessary for the technician to perform an arterial puncture "blindly," merely stabbing the site where the technician considers the best option for obtaining arterial access. The present invention helps to create an augmented pulse that is palpable even in cases of low blood pressure.

Most protocols allow a technician to try three consecutive needle insertions without removing the needle tip beyond the subcutaneous tissue. As the angle of insertion changes within the dermis, the needle slices through the tissue in its path, and may even lacerate the artery. Any change in the angle of needle insertion can inflict severe pain onto a conscious patient.

Because of the structural design of the present invention, a straight, unswerving path of needle insertion into the blood vessel is assured. Currently, the often unsteady hand of the technician is used to guide the needle down into the blood vessel. A nervous hand can become quite jittery, and even a calm hand does not guarantee a straight path of insertion into and out of the vessel. The present invention provides a considerable improvement in this regard; pressing the stabilizer, at the base of the invention, down near the insertion site provides stability to the hand of the technician. The straight shaft, which supports the syringe, vastly improves the likelihood of a direct and controlled line of insertion and extraction of the needle during a catheter insertion procedure, minimizing pain and trauma within the patient's dermal tissues and artery.

Often, the unrestrained nature of the current methods for inserting a catheter into a blood vessel causes the introducer needle to become accidentally extracted from within the blood vessel during a catheter insertion attempt. The present invention prevents this common mishap, by providing a solid, steady shaft on which the syringe is securely held in place during the procedure.

According to standard procedure protocols, a catheter introducer needle should enter an artery at a steady angle of 30 to 45 degrees in relation to the artery; prior art relies on the technician to maintain that angle without any support. A proper angle of needle insertion is assured using the present invention, as a result of the base of the stabilizer fingers being angled in relation to the shaft over which the syringe is maneuvered.

3. Prior Art

Prior art includes devices which help a technician insert a catheter into a blood vessel, and also devices which stabilize a blood vessel during the insertion of a needle therein.

Most of the devices within the realm of prior art do not address the issue of safety adequately. Most catheter insertion devices require the integrated needle to be exposed during much of the procedure; this can be hazardous to technicians and patients if the syringes are handled improperly or unsteadily, as may commonly occur in emergency situations. Needle sticks are the most frequent source of transmission of blood borne disease in healthcare workers. In most of the devices of prior art, the needle is exposed before and after the insertion procedure and there are no means provided to protect personnel from contact with the needle during the procedure. Some devices have disclosed means to withdraw the introducer needle into a safety enclosure after successful insertion of the catheter, but they do not go far enough to prevent injuries and they are difficult to use. Using the current invention, the needle is exposed for only a short period during the entire procedure; the needle is lowered and exposed only after the device has been set over the targeted insertion site. Immediately after the catheter is inserted into the blood vessel, the needle is safely withdrawn out of the blood vessel and back into the protective walls of the needle shield, using only one hand.

Another limitation of prior art is that stability of the device during the procedure is lacking. The stabilizer of the present invention is pressed down near the insertion site to provide stability to the hand of the technician, and a straight path of needle insertion is assured, limiting tissue damage.

Several devices have been proposed for stabilizing a vein for venipuncture, but none of the devices provide proper support for arterial puncture. For arterial puncture, the blood vessel stabilizer portion of the device should be relatively small to accommodate the limited space over the radial artery near the hand, and it should be shaped to facilitate palpation of the targeted puncture site by the technician. The device should be designed to allow a proper angle of needle passage into the artery, and it should be easily removed from the puncture site; it cannot be bound or taped down during use. These features are all present in the current invention.

The present invention may be used on any artery, not just the radial artery. The present invention includes a syringe conveyor to help guide the introducer needle steadily into and out of the artery. The present invention allows the technician to release the pressure over the artery before removing the needle from the insertion site.

The present invention can employ any one of a large variety of existing catheter syringes; the device need not be distributed or sold with a syringe. The present invention further includes an adjustable blood vessel stabilizer to accommodate various sizes of targeted blood vessels.

OBJECTS AND ADVANTAGES

Accordingly, several objects and advantages of the present invention include providing a catheter syringe conveyor device with an integrated needle shield, which:

(a) slidably retains a catheter syringe and renders a straight path of needle passage into and out of the blood vessel.

(b) allows the introducer needle to be immobilized safely within the needle shield.

(c) is held in place using only one of the technician's hands.

(d) helps the technician to keep the tip of the needle steadily within the blood vessel.

(e) shields the technician's fingers from the sharp needle tip during use, to prevent inadvertent injury.

(f) can be used on any individual of any age and size, and on any suitable blood vessel.

(g) can be adapted for use with one of a large variety of catheter syringes, including one with a guide wire.

(h) minimizes the need for multiple attempts to penetrate the blood vessel.

(i) assures a proper angle of needle insertion into a blood vessel.

(j) allows unrestricted blood flow through the ulnar artery when the radial artery is targeted.

(k) holds a blood vessel in place during the insertion of a catheter into the vessel.

(l) isolates an artery and creates an augmented pulse for easy identification of the location of the artery.

(m) is inexpensive to manufacture, simple and intuitive to use, disposable, and light-weight.

(n) allows the technician to regulate the pressure of the device above a blood vessel.

(o) allows the technician to alter the width between each stabilizer finger.

(p) can be reused if cleaned and disinfected properly.

DETAILED DESCRIPTION OF THE INVENTION

Figure 1A:
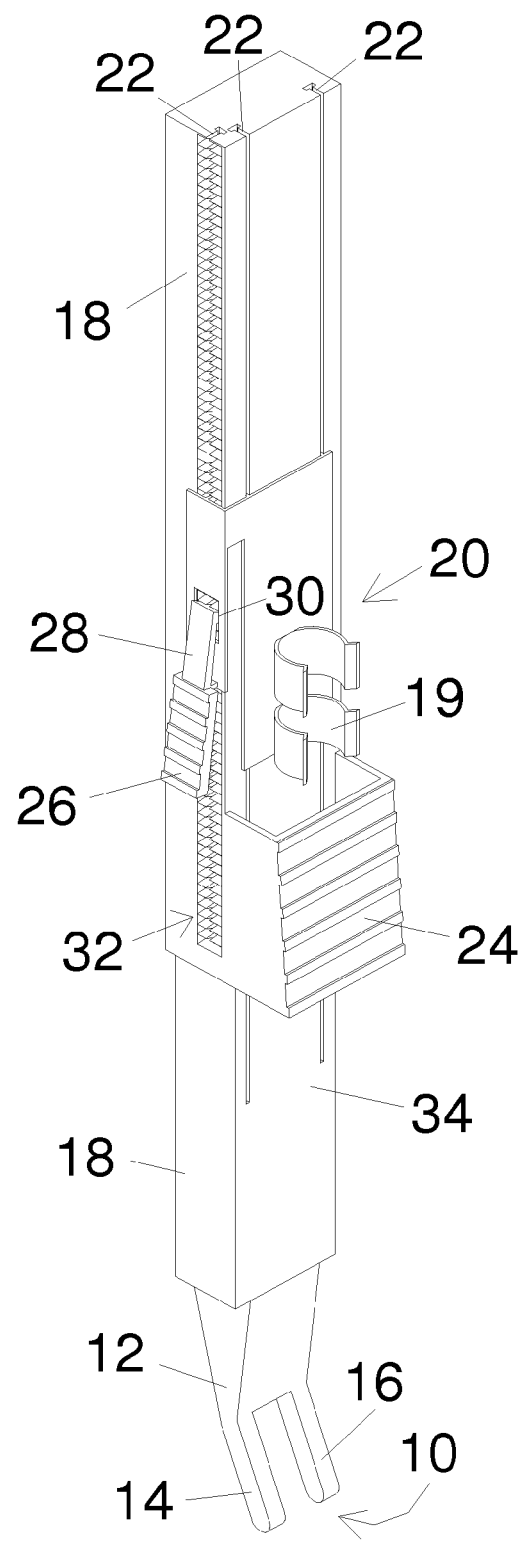
FIG. 1A is an upper left perspective view of one embodiment of the invention with a stabilizer specifically designed for use with arterial punctures, depicting aspects of the invention including the shaft, the needle shield which is permanently mounted to the shaft, the stabilizer attached to the bottom end of the shaft, and the syringe holder slidably situated on the shaft but locked in place by a syringe holder lock.

Referring now to the drawings, FIGS. 1A-5 represent various embodiments and designs of the present invention. Turning first to FIG. 1A, stabilizer 10 includes base 12 and stabilizer fingers 14 and 16; stabilizer fingers 14 and 16 emanate from base 12. A targeted artery is positioned by the technician between stabilizer fingers 14 and 16. Alternatively, only one finger protrudes from base 12; the single finger would hold only one side rather than both sides of a targeted artery. Shaft 18 is attached to base 12. Stabilizer fingers 14 and 16 serve to stabilize shaft 18 and to stabilize a targeted artery during use. Base 12 can be constructed to be detachable from shaft 18 to allow a technician to reuse the device by installing a clean, new stabilizer for each patient. The bottom surface of each stabilizer finger is angled relative to shaft 18. The angle may be 30 degrees, 45 degrees, any angle between 30 and 45 degrees, or any other angle suitable for the procedure. Syringe holder 20 is adapted to retain a number of available catheter syringes. The grasping mechanism 19 on syringe holder 20 can be a simple snap-in mechanism as shown, or it can alternatively be a more complex system in which to lock a syringe. Syringe holder 20 is set in syringe holder track 22 cut out within shaft 18. Syringe holder 20 has legs (not shown) which ride through track 22; they are hidden from view in this image, but are shaped like track 22 to traverse track 22 securely. Alternatively, syringe holder 20 may traverse shaft 18 in any of a number of optional ways, such as within a single track or along a rail. Many catheter syringes are available which include an introducer needle attached to a blood receptacle and a catheter preset over the needle. The blood receptacle component of such a catheter syringe may be placed within syringe holder 20. Needle shield 24 is permanently attached to shaft 18 in this embodiment. A syringe is placed within syringe holder 20 and syringe holder 20 is locked in place so that the needle tip of the installed syringe (not shown) is safely situated within the walls of needle shield 24. The technician can press down over shield 24 to exert pressure over a targeted artery with stabilizer 10. When it is time to lower the syringe, the technician presses finger contact 26 of syringe holder lock 28 to elevate syringe holder locking tooth 30 from within series of notches 32. Once syringe holder locking tooth 30 is freed from within the notch, syringe holder 20 can be moved down shaft 18. The tip of the needle should penetrate the artery when the hub of the catheter is near location 34. The technician can lower the catheter down the needle with one hand and then hold it in place while sliding syringe holder 20 back up the shaft with the other hand. The technician slides syringe holder 20 high enough to leave the tip of the needle once again within the walls of needle shield 24 for safety.

Figure 1B:
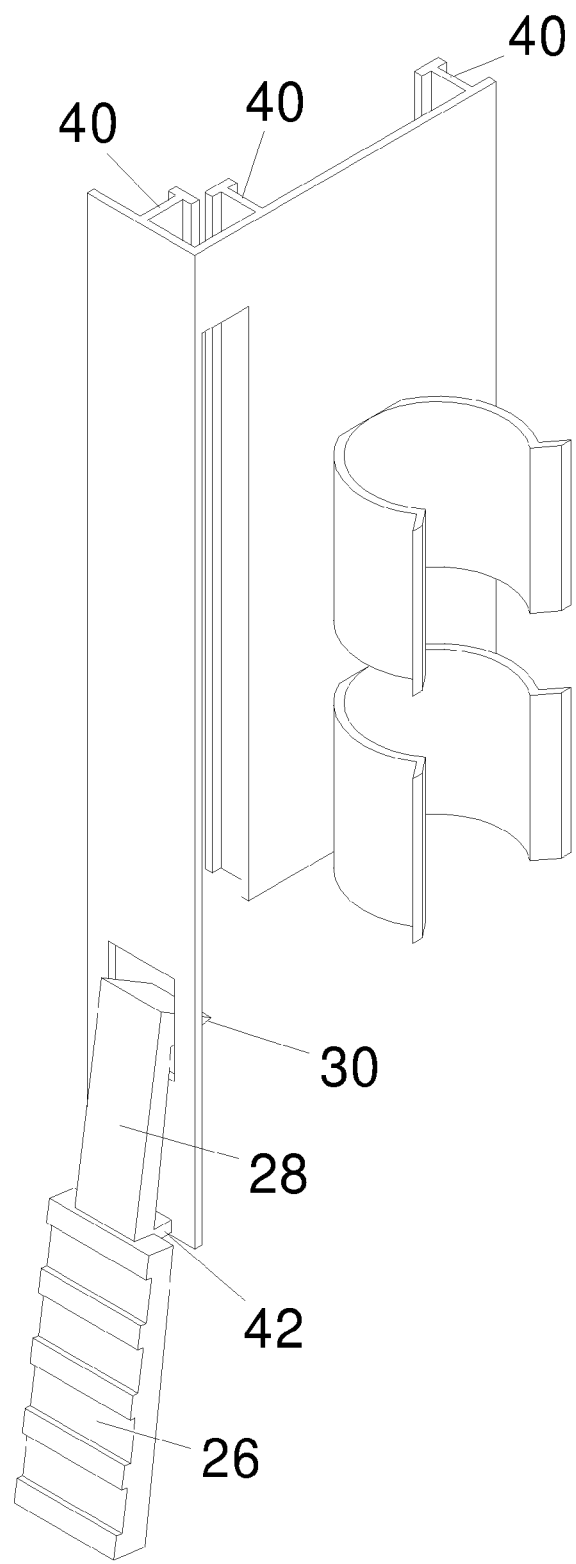
FIG. 1B is an enlarged perspective view of the syringe holder component of the embodiment shown in FIG. 1A.

Turning now to FIG. 1B, syringe holder legs 40 are visible in this image. Also, syringe holder locking tooth 30 is shown more clearly. Syringe holder lock 28 pivots on connection 42 when it is pressed down over finger contact 26.

Figure 2A:
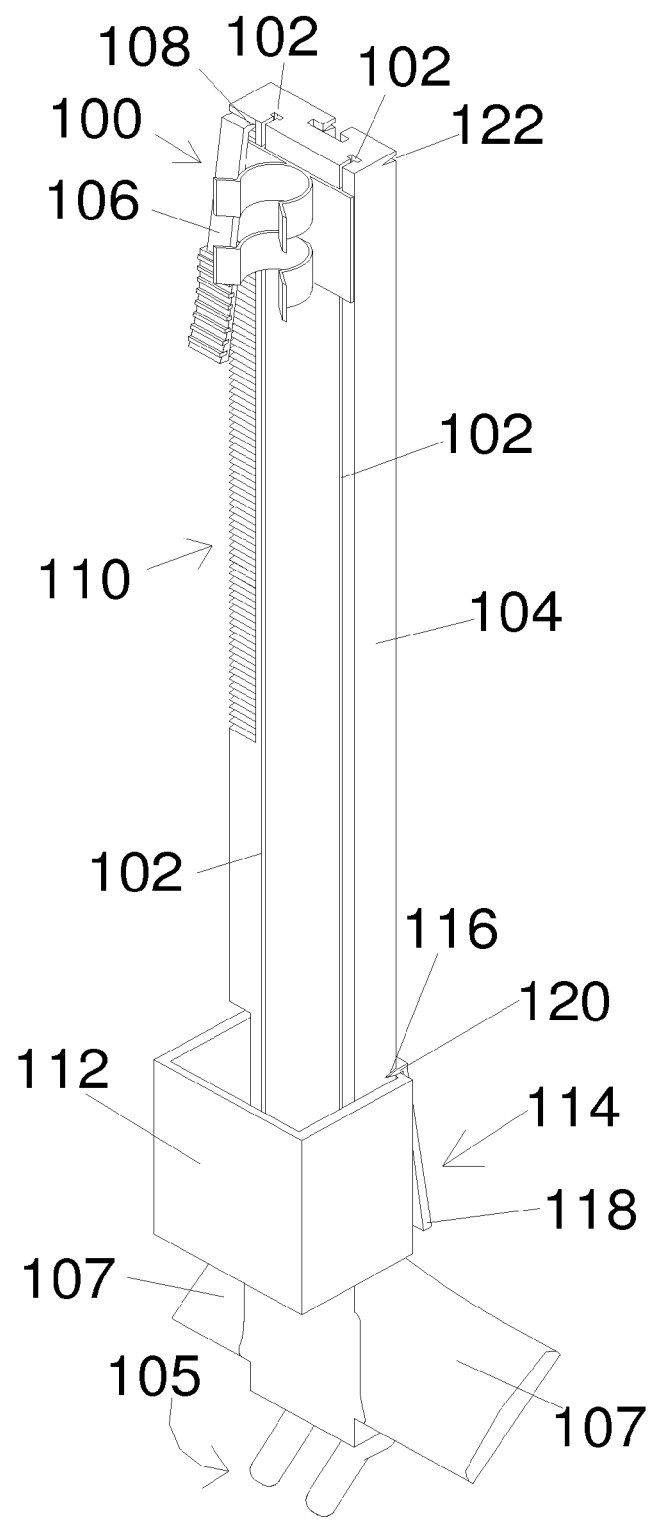
FIG. 2A is an upper left perspective view of an alternative embodiment which has a needle shield which is translatable up and down the shaft of the device, shown here near the bottom end of the shaft.

Turning next to FIG. 2A, needle shield 112 is slidably mounted to shaft 104 in this embodiment. To use this model, a catheter syringe would first be installed within syringe holder 100, which is set within syringe holder track 102. Then, needle shield 112 would be moved up housing shaft 104 and locked in place within upper shield lock receptor 122. The technician would then place stabilizer 105 over the targeted artery, pressing down on finger-hold platform 107, and would then proceed to maneuver syringe holder 100 down shaft 104 until the needle of the attached syringe penetrates the artery. At that time, with the syringe held securely in place within syringe holder 100, the technician would move the catheter down over the needle of the syringe until the hub of the catheter nears the artery. The technician would then raise the syringe back up shaft 104 within syringe holder 100 and lock it there by simply releasing syringe holder lock 106. Syringe holder locking tooth 108 would lock into one notch of series of notches 110. Needle shield 112 would then be lowered down shaft 104 by the technician to cover the exposed needle tip and to prevent inadvertent needle injuries. With the needle tip locked safely within shield 112, the device would be set aside and the technician would secure the catheter within the artery of the patient. FIG. 4A shows shield 112 in the lowered position; it is locked there by shield lock 114. Shield lock tooth 120 engages within lower shield lock receptor 116 which is cut into shaft 104. The technician presses bottom end 118 of shield lock 114 in order to elevate shield tooth 120 from lower lock receptor 116, in order to free shield 112 for travel up or down shaft 104. Shield tooth 120 can also be locked within upper shield lock receptor 122, thereby locking shield 112 at the top end of shaft 104. Each embodiment of this invention allows the technician to reuse the device, provided the device is properly cleaned and disinfected. The device can be made of any durable solid material such as plastic or metal. Rather than a sliding shield, the device can incorporate a shield which is set in a hinge, allowing the technician to swing the shield open prior to the catheter insertion procedure, and swing the shield closed over the needle tip of the syringe, after the insertion.

Figure 2B:
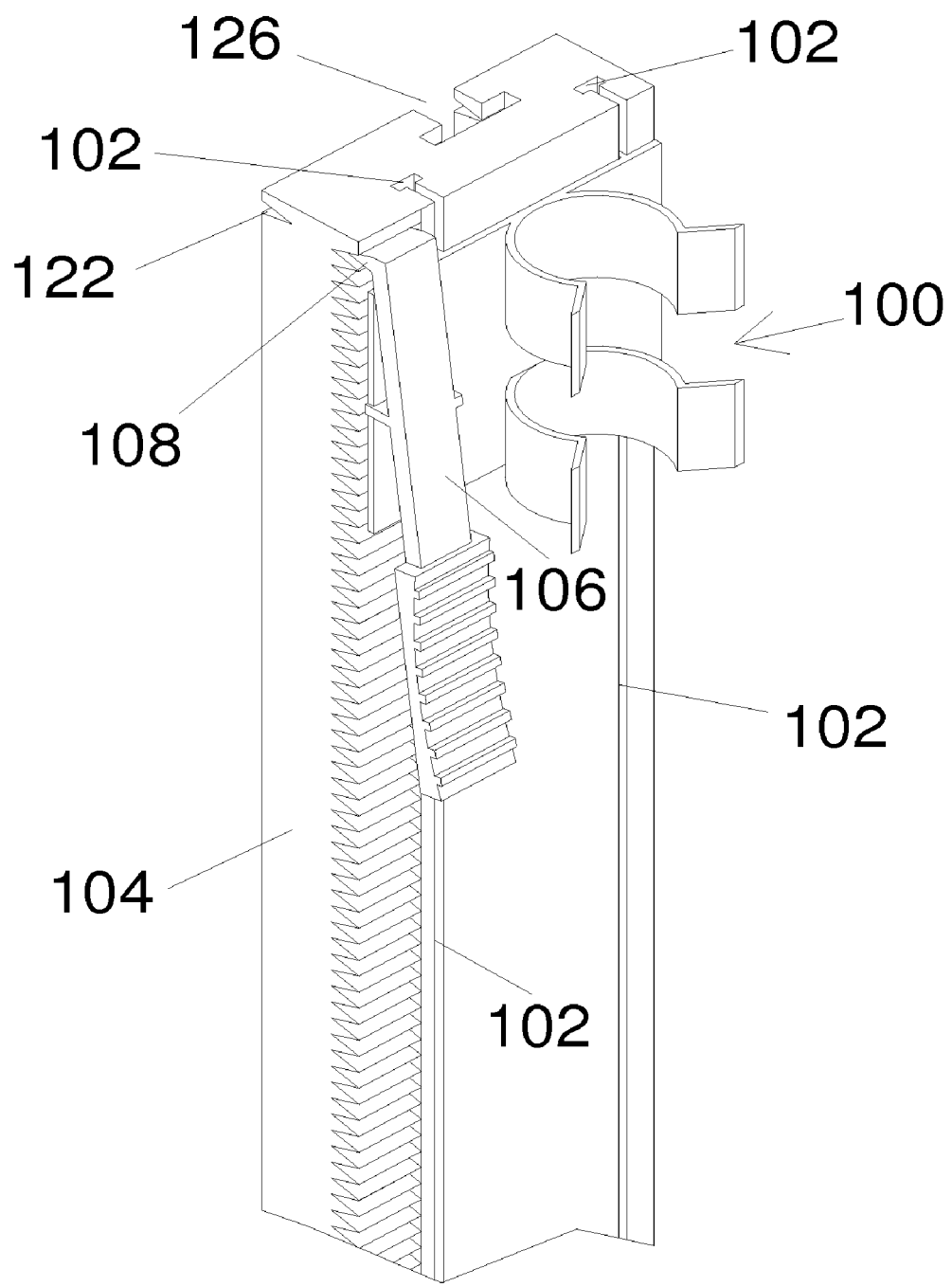
FIG. 2B is an enlarged partial view of the embodiment in FIG. 2A, focusing on the syringe holder, the series of notches, and the top end of the shaft.

Looking at FIG. 2B, many of the components shown in FIG. 2A are shown more visibly. Shield track 126 is cut within shaft 104. The shield has a leg (not shown) which is T-shaped like track 126 to traverse track 126 securely up or down shaft 104.

Figure 3:
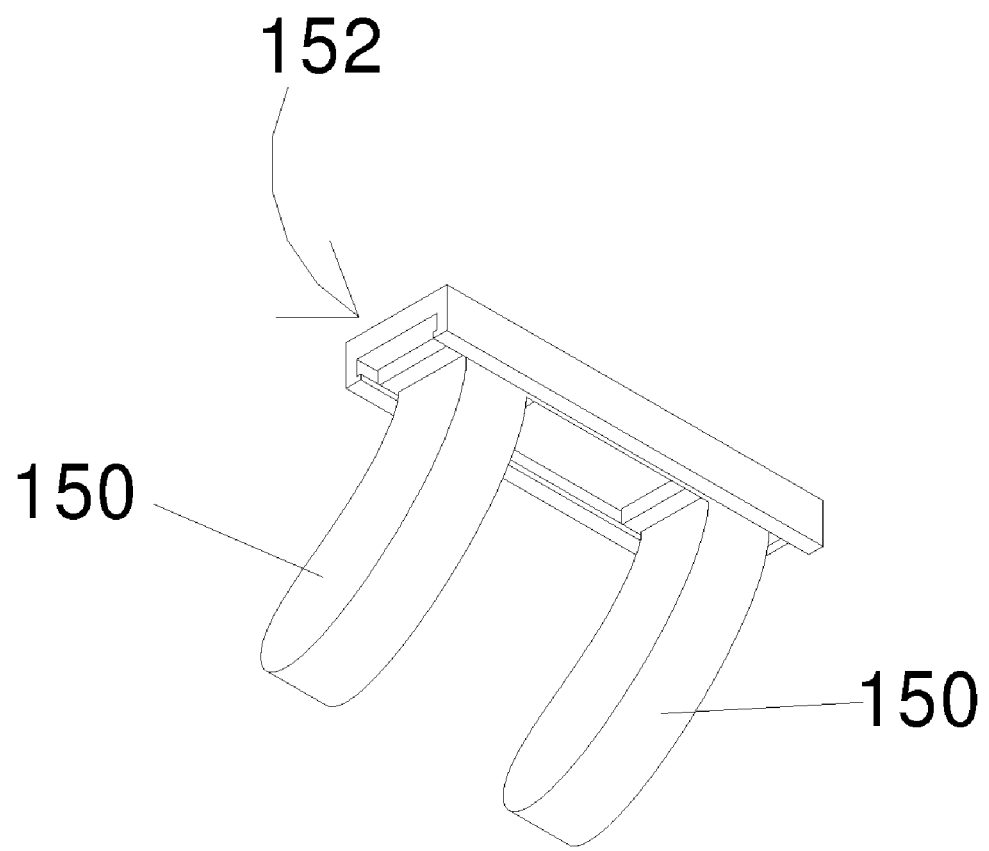
FIG. 3 is an enlarged lower rear perspective view of an alternative stabilizer with each stabilizer finger situated within a track to allow adjustability of the distance between each finger.

Turning to FIG. 3, adjustable stabilizer fingers 150 are slidably situated within stabilizer adjustment track 152 so that the distance between each finger can be altered to accommodate various sizes of targeted blood vessels. It can be designed as a more complex apparatus, such as one which requires the technician to turn a knob to alter the distance between each finger, but a simple one is shown here for ease of illustration.

Figure 4:
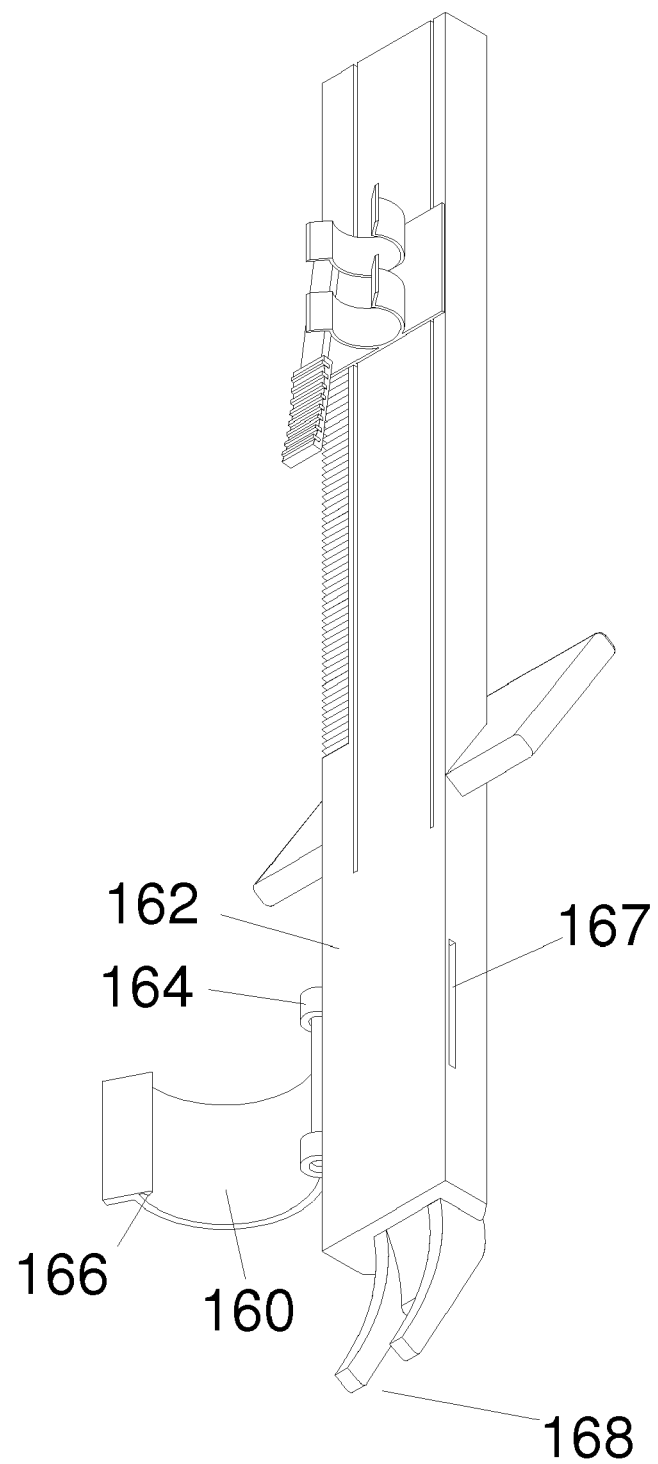
FIG. 4 is a lower right perspective view of an embodiment that has a hinged shield.

Turning now to FIG. 4, either of the previously described embodiments can be easily adapted for use with venous catheters. Vein stabilizer fingers 160 each have a protrusion at the end of the stabilizer finger, between which a vein is situated during a catheter insertion attempt. Since the vein stabilizer fingers contact the patient's skin approximately tangential to the point where the needle penetrates the vein, at point 162, the technician is able to tilt the device during the procedure. The vein stabilizer fingers extend at a very small angle relative to shaft 164, so that after the vein has been penetrated by the needle, the shaft can be brought down nearly parallel to the vein, to allow an effective angle of catheter insertion into the vein. If the targeted vein is properly obstructed by the user beyond the insertion site, the vein should not collapse under the pressure of the fingers.

Figure 5:
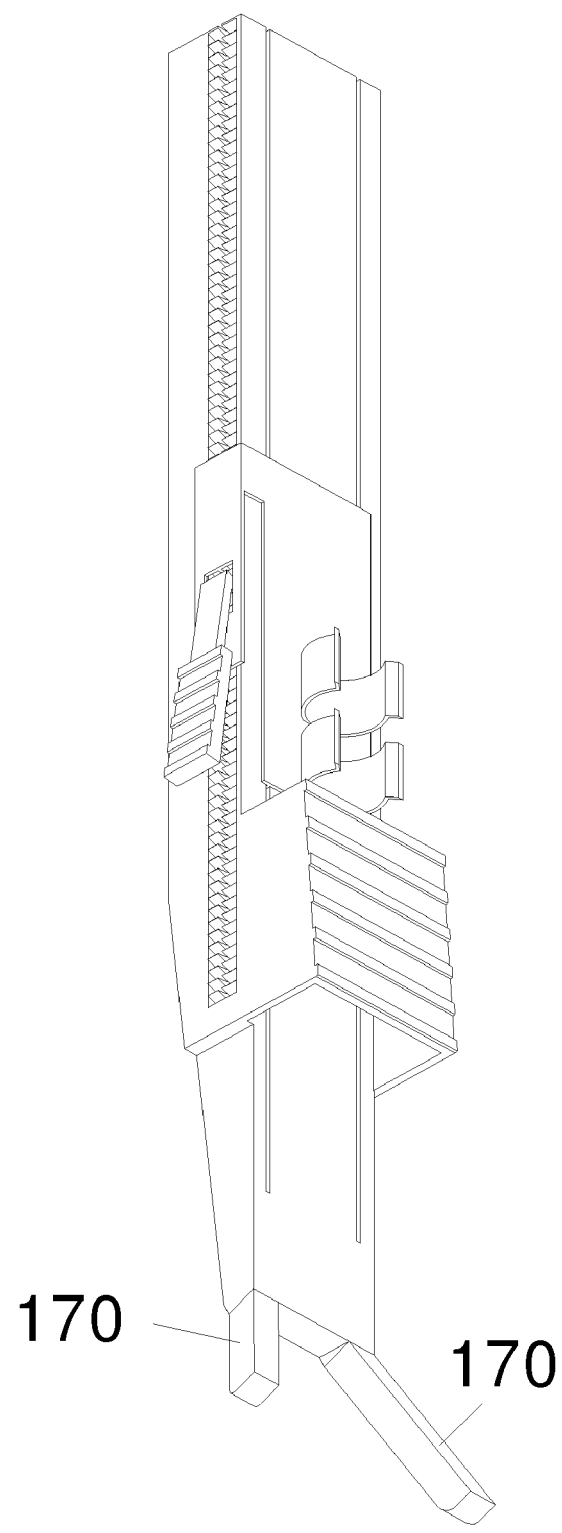
FIG. 5 is an upper left perspective view of an embodiment which has a stabilizer with spaced out stabilizer fingers for preventing obstruction of vascular blood flow near the targeted insertion site.

Turning finally to FIG. 5, this is similar to the embodiment in FIG. 4, except spread out stabilizer fingers 170 are spaced apart more, so as to prevent any possible obstruction of venous blood flow through the targeted vein.

A vascular catheter installer with a syringe holder adapted for use with a catheter syringe is provided for installing an indwelling catheter into a blood vessel. A syringe holder is slidably set on a rigid shaft, allowing a technician to maneuver an attached catheter syringe up and down the shaft. The technician presses down on a finger-hold platform while a stabilizer holds the device in place. The syringe holder can be locked in multiple locations along the shaft and the needle of the syringe can be immobilized within the protective walls of a needle shield for safety.

What is claimed is:

1. An arterial catheter installer comprising:
   a rigid elongated body comprising a distal end, a proximal end, and a top surface;
   an artery stabilizer connected to said proximal end of said elongated body, said artery stabilizer comprising two stabilizer fingers that are spaced apart to depress each side of a targeted artery during use;
   a track formed along part of said elongated body parallel to the axis of said elongated body;
   a catheter syringe holder with at least one leg member that is slidably positioned on said track, said catheter syringe holder being positioned over said top surface of said elongated body, wherein said track positions said catheter syringe holder so that a needle of a catheter syringe that is attached to said catheter syringe holder passes beyond said artery stabilizer to avoid penetrating an occluded section of a targeted artery during an arterial access attempt;
   a series of notches formed along part of said elongated body parallel to said axis of said elongated body;
   a syringe holder lock connected to said syringe holder, said syringe holder lock comprising a tooth that is adapted to engage fixedly with any one of a plurality of notches within said series of notches to allow said syringe holder to be easily positioned fixedly at various locations along said elongated body; and
   a finger-hold platform fixed to said elongated body.

2. The apparatus of claim 1 further comprising a stabilizer finger adjustment mechanism that allows the distance between said stabilizer fingers to be adjusted.

3. The apparatus of claim 2 wherein said adjustment mechanism comprises a stabilizer finger adjustment track.

4. An arterial catheter installer comprising:
   a rigid elongated body comprising a distal end, a proximal end, and a top surface;
   an artery stabilizer means for stabilizing an artery during an arterial access attempt, said artery stabilizer means being connected to said proximal end of said elongated body;
   a track formed along part of said elongated body parallel to the axis of said elongated body;
   a catheter syringe holder with at least one leg member that is slidably positioned on said track, said catheter syringe holder being positioned over said top surface of said elongated body, wherein said track positions said catheter syringe holder so that a needle of a catheter syringe attached to said catheter syringe holder passes beyond said artery stabilizer means to avoid penetrating an occluded section of a targeted artery during an arterial access attempt;
   a lock receptor section formed along part of said elongated body parallel to said axis of said elongated body;
   a syringe holder lock adapted to position said catheter syringe holder fixedly at a plurality of selected locations along said lock receptor section; and
   a finger-hold platform means for manually pressing said elongated body down over a targeted arterial access site, said finger-hold platform means being fixed to said elongated body.

5. The apparatus of claim 4 wherein said syringe holder lock comprises one contact end adapted to be pressed by a user and another lock component end, said syringe holder lock being connected to said syringe holder by a connection that is disposed between both ends of said syringe holder lock and that allows said syringe holder lock to pivot.

6. The apparatus of claim 4 wherein said artery stabilizer means comprises two artery stabilizer fingers, each artery stabilizer finger comprising a narrow bottom surface that is spaced apart from the other to depress each side of a targeted artery during use.

7. A vascular catheter installer comprising:
   A rigid elongated body comprising a distal end, a proximal end, and a top surface;
   a stabilizer means for stabilizing said elongated body against the skin of a patient during use, said stabilizer means being connected to said proximal end of said elongated body;
   a track formed along part of said elongated body parallel to the longitudinal axis of said elongated body;
   a catheter syringe holder with at least one leg member that is slidably positioned on said track, said catheter syringe holder being positioned over said top surface of said elongated body;
   a series of notches formed along part of said elongated body parallel to said longitudinal axis of said elongated body;
   a syringe holder lock connected to said syringe holder, said syringe holder lock comprising a locking tooth that is adapted to engage fixedly with any one of a plurality of notches within said series of notches to allow said syringe holder to be easily positioned fixedly at various locations along said elongated body; and
   a finger-hold platform means for manually pressing said elongated body down over a targeted vascular access site, said finger-hold platform means being fixed to said elongated body.

8. The apparatus of claim 7 wherein said syringe holder lock comprises one contact end adapted to be pressed by a user and another locking tooth end, said syringe holder lock being connected to said syringe holder by a connection that is disposed between both ends of said syringe holder lock and that allows said syringe holder lock to pivot.

* * * * *